United States Patent [19]
Raths et al.

[11] Patent Number: 5,936,107
[45] Date of Patent: Aug. 10, 1999

[54] PROCESS FOR THE PRODUCTION OF FATTY ACID POLYETHYLENE GLYCOL ESTERS

[75] Inventors: Hans-Christian Raths, Monheim; Ansgar Behler, Bottrop, both of Germany; Norman Milstein, Montgomery, Ohio

[73] Assignee: Henkel Kommanditgesellschaft auf Aktien, Duesseldorf, Germany

[21] Appl. No.: 08/767,123

[22] Filed: Dec. 9, 1996

[51] Int. Cl.$^6$ ..................... C07C 51/00
[52] U.S. Cl. ............................. 554/149
[58] Field of Search ............... 554/149

[56] References Cited

U.S. PATENT DOCUMENTS 3,884,946  5/1975  Sung et al. .................. 260/400
4,722,811  2/1988  Godwin ....................... 554/149

*Primary Examiner*—Gary Geist
*Assistant Examiner*—Deborah D Carr
*Attorney, Agent, or Firm*—Wayne C. Jaeschke; John E. Drach; Steven J. Trzaska

[57] ABSTRACT

Fatty acid polyethylene glycol esters of the formula (I):

$$R^1CO(CH_2CH_2O)_nH \qquad (I)$$

wherein $R^1CO$ is a linear or branched, aliphatic, saturated and/or unsaturated acyl group having from about 6 to about 22 carbon atoms and n is a number from 0.5 to 1.5 are made by reacting ethylene oxide and a fatty acid in the presence of an alkanolamine in a homogeneous reaction medium.

9 Claims, No Drawings

PROCESS FOR THE PRODUCTION OF FATTY ACID POLYETHYLENE GLYCOL ESTERS

BACKGROUND OF THE INVENTION

1. Field of the Invention

This invention relates to a process for the production of fatty acid polyethylene glycol esters by ethoxylation of fatty acids in the presence of alkanolamines.

2. Statement of the Related Art

The addition of alkylene oxides to CH-acidic compounds such as, for example, fatty alcohols, alkylphenols, fatty amines or even fatty acids is among the industrially established processes for the production of nonionic surfactants. These reactions are normally carried out in the presence of homogeneous basic catalysts such as, for example, sodium hydroxide or sodium methylate. However, alkoxylation is not a selective reaction, but one which follows statistics. Accordingly, the average degree of alkoxylation can at best be estimated from the molecular ratio in which the CH-acidic compound and the alkylene oxide are used. In practice, however, the maximum of the resulting homolog distribution—particularly at low alkoxylation ratios—is never to be found in the average degree of alkoxylation, but is generally displaced towards higher homologs.

Attempts have been made to counteract this unwanted effect by using catalysts with a higher selectivity which, overall, lead to alkoxylates, particularly ethoxylates, having a narrower ("restricted") homolog distribution. These products are often referred to in the literature as narrow-range ethoxylates. Preferred homogenous catalysts for this purpose are alkaline earth metal salts such as, for example, barium phosphate or strontium ether carboxylates. Heterogeneous catalysts such as, for example, calcined hydrotalcites are also suitable.

However, the efforts which have hitherto been made in regard to the ethoxylation of fatty acids are still unsatisfactory. Above all in the production of fatty acids with low degrees of ethoxylation, particularly fatty acid +1 EO adducts, which are of interest as precursors for the synthesis of ether sulfate surfactants with an isethionate-like structure, the selectivities obtained are unsatisfactory. Apart from an unwanted content of homologs with a relatively high degree of ethoxylation, significant quantities of polyethylene glycol and diesters are also formed.

Accordingly, the problem addressed by the present invention was to provide an improved homogeneous chemical process for the production of fatty acid polyglyol esters, particularly fatty acids with low degrees of ethoxylation, which would be distinguished by improved selectivity.

SUMMARY OF THE INVENTION

Fatty acid polyethylene glycol esters of the formula (I):

wherein $R^1CO$ is a linear or branched, aliphatic, saturated and/or unsaturated acyl group having from about 6 to about 22 carbon atoms and n is a number from 0.5 to 1.5 are made by reacting ethylene oxide and a fatty acid in the presence of an alkanolamine in a homogeneous reaction medium.

DESCRIPTION OF THE PREFERRED EMBODIMENTS

The present invention relates to a process for the production of fatty acid polyethylene glycol esters corresponding to formula (I):

in which $R^1CO$ is a linear or branched, aliphatic, saturated and/or unsaturated acyl group containing 6 to 22 carbon atoms and n is a number of 0.5 to 1.5, by homogeneous base-catalyzed addition of ethylene oxide to fatty acids, characterized in that the ethoxylation is carried out in the presence of alkanolamines.

It has surprisingly been found that alkanolamines, particularly triethanolamine, are highly selective catalysts for the ethoxylation of fatty acids, particularly when homologs with low degrees of ethoxylation are to be produced.

Fatty Acids

Fatty acids in the context of the invention are aliphatic carboxylic acids corresponding to formula (II):

in which $R^1CO$ is an aliphatic, linear or branched acyl group containing 6 to 22 and preferably 12 to 18 carbon atoms and 0 and/or 1, 2 or 3 double bonds. Typical examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms such as, for example, coconut oil, palm oil, palm kernel oil or tallow fatty acid.

Alkanolamines

Typical examples of alkanolamines suitable for use as basic catalysts are monoethanolamine, diethanolamine and, preferably, triethanolamine. The alkanolamines are normally used in quantities of 0.1 to 3% by weight and preferably in quantities of 0.5 to 1.5% by weight, based on the fatty acids.

Ethoxylation

The ethoxylation may be carried out in known manner. Typically, the fatty acid and the catalyst are introduced into a stirred autoclave which is freed from traces of water before the reaction by alternate evacuation and purging with nitrogen. The fatty acid is then reacted with the ethylene oxide in a molar ratio of 1:0.5 to 1:1.5. The ethylene oxide may be introduced into the autoclave in portions by a siphon after heating. The fatty acids are preferably reacted with 1 mole of ethylene oxide. The ethoxylation may be carried out at temperatures of 80 to 180° C. and preferably at temperatures of 100 to 120° C. under autogenous pressures of 1 to 5 bar and preferably 2 to 3 bar. After the end of the reaction, it is advisable to stir the reaction mixture for a certain time (15–90 mins.) at the reaction temperature in order to complete the conversion. The autoclave is then cooled and vented and, if desired, acids such as, for example, lactic acid or phosphoric acid are added to the product in order to neutralize the basic catalyst.

The following examples are meant to illustrate but not to limit the invention.

EXAMPLE

Example 1

200 g (1 mole) of technical lauric acid were introduced into a 1-liter stirred autoclave, followed by the addition of 2 g of triethanolamine (corresponding to 1% by weight, based on lauric acid). The autoclave was alternately evacuated and purged with nitrogen three times to remove traces of water which could lead to the formation of polyethylene glycol. After the reaction mixture had been purged with nitrogen for the last time, the autoclave was closed and heated to 100° C. and 44 g (1 mole) of ethylene oxide were introduced in portions under a maximum pressure of 5 bar. On completion of the reaction—recognizable by the fact that the pressure again fell to a value of 1.2 bar and then remained constant—the reaction mixture was stirred for 30 mins. and then cooled and vented. The basic catalyst was neutralized by addition of a corresponding quantity of lactic acid. The characteristic data of the lauric acid +1 EO adduct are set out in Table 1.

Example 2

The procedure was as in Example 1, except that the reaction mixture was stirred for 60 minutes. The results are set out in Table 1.

Examples 3 and 4

Example 2 was repeated with (3) 0.5% by weight and (4) 1% by weight of triethanolamine. The results are set out in Table 1.

Examples 5 and 6

Example 2 was repeated at (5) 80° C. and (6) 90° C. The results are set out in Table 1.

Examples 7 to 9

Example 2 was repeated using 1 mole of $C_{12/14}$ cocofatty acid (7), 1 mole of $C_{12/18}$ cocofatty acid (8) and 1 mole of $C_{16/18}$ tallow fatty acid (9) and 1 mole of ethylene oxide. The results are set out in Table 1.

Comparison Example C1

Example 1 was repeated with 0.5% by weight of calcined hydrotalcite as catalyst at 145–160° C. The results are set out in Table 1.

What is claimed is:

1. A process for the production of fatty acid polyethylene glycol esters of the formula (I):

$$R^1COO(CH_2CH_2O)_nH \qquad (I)$$

wherein $R^1CO$ is a linear aliphatic, saturated and/or unsaturated acyl group having from about 6 to about 22 carbon atoms and n is a number from 0.5 to 1.5 which comprises reacting ethylene oxide and a fatty acid in the presence of an alkanolamine in a homogenous reaction medium and wherein the reaction is carried out at a temperature of from about 80 to about 120° C.

2. The process of claim 1 wherein said fatty acid is a compound of the formula (II):

$$R^1COOH \qquad (II)$$

wherein $R^1CO$ is a linear aliphatic, saturated and/or unsaturated acyl group having from about 6 to about 22 carbon atoms.

3. The process of claim 1 wherein the mole ratio of ethylene oxide to fatty acid is from about 1:0.5 to about 1:1.5.

4. The process of claim 1 wherein said alkanolamine is monoethanolamine, diethanolamine or triethanolamine.

5. The process of claim 4 wherein said alkanolamine is triethanolamine.

6. The process of claim 1 wherein the amount of alkanolamine is from about 0.1 to about 3% by weight based on the weight of said fatty acid.

7. The process of claim 1 wherein said temperature is from about 100° C. to about 120° C.

8. The process of claim 1 wherein said process is carried out at a pressure of from about 1 to about 5 bar.

9. The process of claim 8 wherein said pressure of from about 2 to about 3 bar.

TABLE 1

| Composition of the fatty acid + EO adducts (quantities in % by weight) | | | | | | | | | | |
|---|---|---|---|---|---|---|---|---|---|---|
| | 1 | 2 | 3 | 4 | 5 | 6 | 7 | 8 | 9 | C1 |
| Polyethylene glycol content | <0.1 | <0.1 | <0.1 | <0.1 | <0.1 | <0.1 | <0.1 | <0.1 | <0.1 | 1.1 |
| Free fatty acid | 4.3 | 5.0 | 9.9 | 6.4 | 43.3 | 18.0 | 3.8 | 6.4 | 6.7 | 12.0 |
| Fatty acid + 1 EO adduct | 89.0 | 87.3 | 79.6 | 85.0 | 52.1 | 75.5 | 86.4 | 85.0 | 84.2 | 45.0 |
| Fatty acid + 2 EO adduct | 2.7 | 2.8 | 4.0 | 2.1 | 1.9 | 2.8 | 3.0 | 2.1 | 2.7 | 2.0 |
| Fatty acid + 3 EO adduct | 0.1 | <0.1 | <0.1 | <0.1 | <0.1 | <0.1 | <0.1 | <0.1 | <0.1 | 0.3 |
| Diesters | 6.3 | 3.8 | 5.0 | 4.3 | 1.1 | 1.7 | 5.6 | 4.3 | 4.6 | 39.2 |
| Higher homologs | | | | | To 100 | | | | | |

* * * * *